United States Patent [19]

Lipscher

[11] 4,082,084
[45] Apr. 4, 1978

[54] PORTABLE DIAGNOSTIC DEVICE

[75] Inventor: Ervin Lipscher, Budapest, Hungary

[73] Assignee: Medicor Muvek, Budapest, Hungary

[21] Appl. No.: 651,599

[22] Filed: Jan. 22, 1976

[30] Foreign Application Priority Data

Jan. 31, 1975 Hungary ............................ ME 1832

[51] Int. Cl.² .................................................. A61B 5/00
[52] U.S. Cl. ................................................... 128/2 D
[58] Field of Search ............. 128/2 D, 2 H, 2 R, 2 Z,
128/2.05 A, 2.05 B, 2.05 M, 2.05 P, 2.05 Q, 2.05
R, 2.05 T, 2.06 A, 2.06 F, 2.06 R, 2.08, 2.1 B,
2.1 Z; 312/209, 243, 244, 251, 293

[56] References Cited

U.S. PATENT DOCUMENTS

| 3,374,461 | 3/1968 | Anderholm et al. | 128/2 D |
| 3,392,241 | 7/1968 | Weiss et al. | 128/2 Z |
| 3,766,908 | 10/1973 | Haynes | 128/2 H |
| 3,857,383 | 12/1974 | Sommerfeld et al. | 128/2 D |
| 3,865,101 | 2/1975 | Saper et al. | 128/2.06 R |
| 3,908,640 | 9/1975 | Page | 128/2.05 T |
| 3,948,250 | 4/1976 | Weisman | 128/2.06 F |

Primary Examiner—William E. Kamm
Attorney, Agent, or Firm—Young & Thompson

[57] ABSTRACT

A portable diagnostic device, particularly for medical field-examinations comprising a case-like housing in which replaceable electronic examining units are arranged serving for the examination of different physiological functions and/or conditions. The housing comprises an electronic power supply feeding each of the electronic examining units, a common display receiving the output signals of the examining units and electrical connectors providing electrical connections between the housing and each of the examining units. The inner room of the housing is divided into two separate parts, the first of which is arranged in a modular system and accommodates slide-in examining units, while the second part serves to accommodate the accessory means required for the examinations.

2 Claims, 3 Drawing Figures

PORTABLE DIAGNOSTIC DEVICE

The invention relates to a portable diagnostic device, particularly for field-examinations, which can provide quick, correct and many-sided diagnostic information on the vital functions and/or conditions of the examined persons even under unfavorable field environmental circumstances.

The development and application of the portable types of diagnostic devices have recently come more and more into the foreground. Portable case-like like devices have already been worked out for the examination of almost every vital function, which can well be used also for field-examinations. Such instruments are e.g. the portable electrocardioscopes, thermometers, pulse rate meters, blood pressure meters, etc. The portable electrocardioscopes of the Austrian Company Hugo Sachs and that of the Medicor Works, Budapest are for example available on the market.

Although these instruments proved to be good for individual examinations, they could not meet the complexity of requirements raised by the demands of field-examinations.

In most of the cases there is a need even under unfavorable field conditions to simultaneously examine or control a plurality of vital functions and to obtain information about several condition data of the examined patient as quick as possible. The work of installation of several portable instruments is a complicated task which takes much time, the measuring cables of the instruments can easily get mixed up with each other which may result in malfunctions and the necessary instruments must be preselected prior to visiting the examination site. The greatest disadvantage of such installed systems is the loss of the portable character because a person can not carry and handle more than one, or at most two of such case-like instruments.

The object of the invention is to provide a portable diagnostic device which can fully meet the requirements of field-examinations and can easily be installed and handled.

This object is attained by providing a portable diagnostic device comprising according to invention a plurality of replaceable electronic units each of which serves for the examination of different physiological functions and/or conditions, these units being arranged in and integral with a case-like housing. The housing comprises an electronic power supply feeding each of the electronic examining units, a common display receiving the output signals of the examining units, and electrical connectors providing electrical connections between the housing and the respective examining units. The inner space of the case-like housing comprises at least two separated spaces, the first space serving for the accommodation of all of the electronic examining units, while the second space accommodates all the accessory means required for the examinations. The first space is arranged in a modular system to receive at least four electronic examining units. The replaceable electronic examining units are selected and arranged to comply with the complexity of the existing examination demands.

A preferred embodiment of the diagnostic device comprises an electrocardioscope, an electroencephalographical oscilloscope, a thermometer, a pulse rate meter, a spirometer, a blood pressure meter, an audiometer and a reaction time meter.

Each of the electronic examining units having a self supporting chassis and an independent electronic circuitry, these units are arranged in a modular system and are assembled in a practical geometric order beside each other.

A preferred embodiment of the invention comprises a common display which is connected via a display function selecting switch to the measuring terminals of the connector receptacles receiving the connector plugs of the individual electronic examining units.

The combination of the individually known examining units into a common portable diagnostic system immediately eliminates the specific problems connected with the field-examinations and opens the way for the introduction of numerous essential constructional rationalizations. By this system the portable feature is maintained and the need for the separate installation and layout of the individual measuring apparatuses and for the complicated arrangement of the measuring and examining units which are to be attached to the examined persons is eliminated. By means of the integration of the individual apparatuses numerous distinct housings can be eliminated, while in the single common housing a common display can be arranged which increases the visuality and lucidity of the examination and greatly decreases the possibility of false readings of the measuring results.

Depending on the actual purpose of the examinations the same case-like housing can contain a wide range of various functional units (if some minor modifications are carried out in the wiring). This way the diagnostic device can actually "adapt itself" to the medical task which is to be solved thereby.

The diagnostic device can be operated either from the mains power or from a battery. It can easily be transported by its handle and it can be set up on a table.

The invention will now be described in connection with a preferred embodiment wherein reference is made to the attached drawings. In the drawings.

Figure 1:
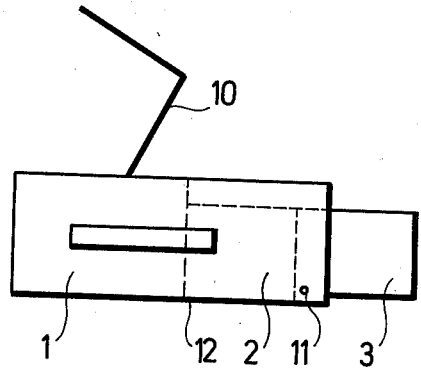
FIG. 1 shows the schematic side elevation view of the diagnostic device with opened casing lid.
Figure 2:
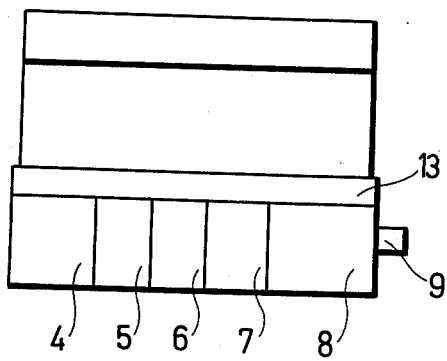
FIG. 2 shows the front elevation view of the device shown in FIG. 1.
Figure 3:
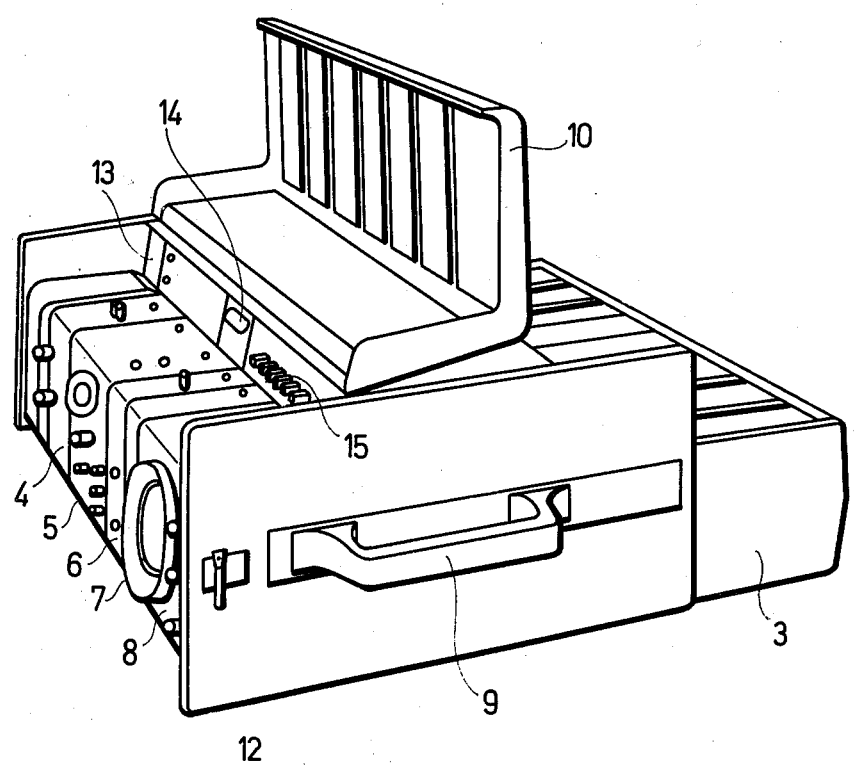
FIG. 3 shows the perspective view of the device.

Referring now to FIGS. 1 and 2 the diagnostic device is shown with opened casing lid 10 and with swung out accessory storage 3. During transport the device has a suitcase like shape which has a handle 9 on its end by which it can easily be carried by hand. The elements that can be swung out or opened i.e. the casing lid 10 and the accessory storage 3 are protected by catches (not shown in the drawings) from inadvertent opening.

It can be seen from the side view that the inner space of the housing 12 of the device consists of two separate parts. The first space 1 serves to accommodate the examining units 4, 5, 6, 7 and 8 and the common electronic circuits (power supply, display, common amplifiers, etc.). There is behind the first space 1 within the rear part of the device the second space 2 serving to accommodate the accessory means required for the operation of the device. The accessory means are located in appropriate compartments within the storage 3 which can be swung out around a hinge 11.

The width of the examining units 4, 5, 6, 7 and 8 was selected to be in accordance with a predetermined modular spacing. The width of the examining unit 8 e.g. an electrocardioscope is just twice as big as that of the other units. The height of the examining units is smaller than the overall height of the device and on the free upper surface of these units handling and signalling means as well as connector sockets are situated. Each examining unit has this way an "L" shaped face-plate which makes it possible for these examining units that, however small mechanical dimensions they have, they represent fully efficient measuring instruments wherein all the means (e.g. knobs, sockets, instruments) required for the operation and adjustment are located in logically understandable and lucid geometric configurations.

To the rear of the upper surface of the examining units there is provided a vertical front plate 13 on the housing in which a common digital display 14 and the common adjusting means 15 (e.g. buttons, keys, knobs, etc.) are located. This arrangement facilitates the work of the operator.

The examining units 4, 5, 6, 7 and 8 are located in the first space 1 of the housing 12 arranged in a modular system. The housing 12 comprises multipole connector sockets receiving respective connector plugs mounted on the rear surface of the examining units.

If the examining units are pulled out from the housing 12, they cannot be operated because their electrical connections are broken. These units receive their electrical power and their control and operating voltages from the power supply and the adjusting means located in the common housing. The examining units transmit the results of the examinations through the connectors to the common electronic circuitry located in the housing.

The results of the examinations are coupled to the common display 14 through a display function selecting switch having contact terminals connected to the measuring output terminals of the multipole connectors. The number of the positions of the function selecting switch is preferably equal to the number of the different kind of examinations that can be carried out by the device.

Each examining unit may be adaptable for the examination of more than one physiological function and/or state. The modular constructional arrangement of the examining units offers the possibility for selecting an assembly thereof in the housing which corresponds to the actual diagnostic tasks that must be carried out by the device. The invention cannot of course be limited to any specific arrangement of the examining units which may comprise an electrocardioscope, an EEG unit, different kinds of thermometers, pulse-rate meters, blood pressure meters, instruments for blood counting, an audiometer, a spirometer, etc. If the actual diagnostic task changes, the examining units can be partly or fully replaced by other ones and re-assembled and the device can in this way be adapted to the new demands. This adaptation requires only some minor modifications in the wiring of the multipole connector sockets associated with the examination units, and a universal wiring arrangement of these connectors can also be worked out by which the examining units can be interchanged without effecting any modifications in the wiring.

The portable diagnostic device facilitates the performance of field-examinations (i.e. examinations that can be carried out everywhere without any local limitations, for example in vehicles, at the site of given events, etc.) because it provides room in the storage 3 for the accessories required for the examinations which are located in well designed cells in a lucid arrangement that increases the speed of the preparatory phases of the examinations and prevents the accessories from being accidentally interchanged. From this arrangement the operator can easily detect if some of the accessories are missing.

What is claimed is:

1. A portable diagnostic device, particularly for medical field examinations, comprising a portable carrying case having a handle thereon for carrying the case, and in the case a plurality of replaceable electronic examining units for the examination of different physiological functions and/or conditions, an electronic power supply in the case for feeding each of the electronic examining units, a common display carried by the case receiving output signals of the examining units, electrical connectors providing electrical connections between electrical circuits in the case and electrical circuits in the examining units, the interior of the case comprising at least two separated spaces, a first said space accommodating all of the electronic examining units, a second said space accommodating accessories for the examination, there being at least four said electronic examining units in said first space, a portion of the outside of said portable carrying case being comprised by an L-shaped lid mounted for swinging movement on and relative to said case between a raised position in which said lid rests on said case and a closed position in which said lid closes said first space within said case, said lid in said closed position overlying said examining units, each said examining unit having an L-shaped face plate defining the upper side and the front of said unit, there being an upright front plate between said upper sides of said examining units and the axis of swinging movement of said lid on said case.

2. A portable diagnostic device as claimed in claim 1, said common display being disposed on said vertical front plate.

* * * * *